United States Patent [19]

Michel et al.

[11] Patent Number: 5,472,022

[45] Date of Patent: Dec. 5, 1995

[54] INJECTION PEN SOLUTION TRANSFER APPARATUS AND METHOD

[75] Inventors: Peter Michel, Burgdorf, Switzerland; Robert S. Freeman, Weston, Mass.; James Q. Oeswein, El Granada, Calif.

[73] Assignee: Genentech, Inc., South San Francisco, Calif.

[21] Appl. No.: 146,313

[22] Filed: Nov. 2, 1993

[51] Int. Cl.$^6$ .............................. B65B 1/04; B65B 3/04
[52] U.S. Cl. ................... 141/1; 141/23; 141/21; 141/27; 141/311 R; 141/318; 141/319; 141/329; 141/330; 141/383; 604/82; 604/232; 604/463; 604/415
[58] Field of Search ................. 141/1, 2, 18, 19, 141/21, 22, 23, 25, 26, 27, 318, 319, 320, 322, 329, 330, 383, 98; 222/386; 604/407, 207, 82, 403, 411, 412, 414, 415, 416, 905, 228, 229, 232, 233, 234, 235

[56] References Cited

U.S. PATENT DOCUMENTS

| | | | |
|---|---|---|---|
| 3,110,309 | 11/1963 | Higgins | 604/232 |
| 3,330,281 | 8/1964 | Visser | 141/27 |
| 4,585,439 | 4/1986 | Michel | 604/155 |
| 4,701,165 | 10/1987 | DeHaitre | 604/228 |
| 4,865,591 | 9/1989 | Sams | 604/186 |
| 4,883,472 | 11/1989 | Michel | 604/208 |
| 5,017,190 | 5/1991 | Simon et al. | 604/207 |
| 5,032,114 | 7/1991 | Olovson | 604/110 |
| 5,171,214 | 12/1992 | Kolber et al. | 604/905 |
| 5,226,896 | 7/1993 | Harris | 604/211 |
| 5,232,459 | 8/1993 | Hjertman | 604/208 |

FOREIGN PATENT DOCUMENTS

| | | | |
|---|---|---|---|
| 0616208 | 3/1961 | Canada | 604/403 |
| EP89/01236 | 10/1989 | European Pat. Off. | |
| 0918100 | 2/1963 | United Kingdom | 604/415 |

*Primary Examiner*—Henry J. Recla
*Assistant Examiner*—Timothy L. Maust
*Attorney, Agent, or Firm*—Skjerven, Morrill, MacPherson, Franklin & Friel; Forrest E. Gunnison; Philip J. McKay

[57] ABSTRACT

An injection pen apparatus (30) for medicament injection including a medicament cartridge assembly (31) formed to receive and contain a medicament therein. A holding sleeve (34) is provided which is dimensioned to receive the medicament cartridge assembly (31) therein which mates with a solution transfer device (35) including an axially movable displacement rod (36). The injection pen apparatus (30) further includes a coupling mechanism (37) removably coupling the solution transfer device (35) to both a plunger (32) slidably movable in the cartridge (33) and to the holding sleeve (34). A sleeve mounting assembly (40) of the coupling mechanism (37) removably mounts the coupling mechanism to the holding sleeve (34). A locking device (41) is included which is formed and dimensioned to require joining of the displacement rod (36) relative the sleeve mounting assembly (40) after uncoupling of the rod from the plunger (32) and before uncoupling of a remainder of the solution transfer device (35) from the holding sleeve (34).

32 Claims, 3 Drawing Sheets

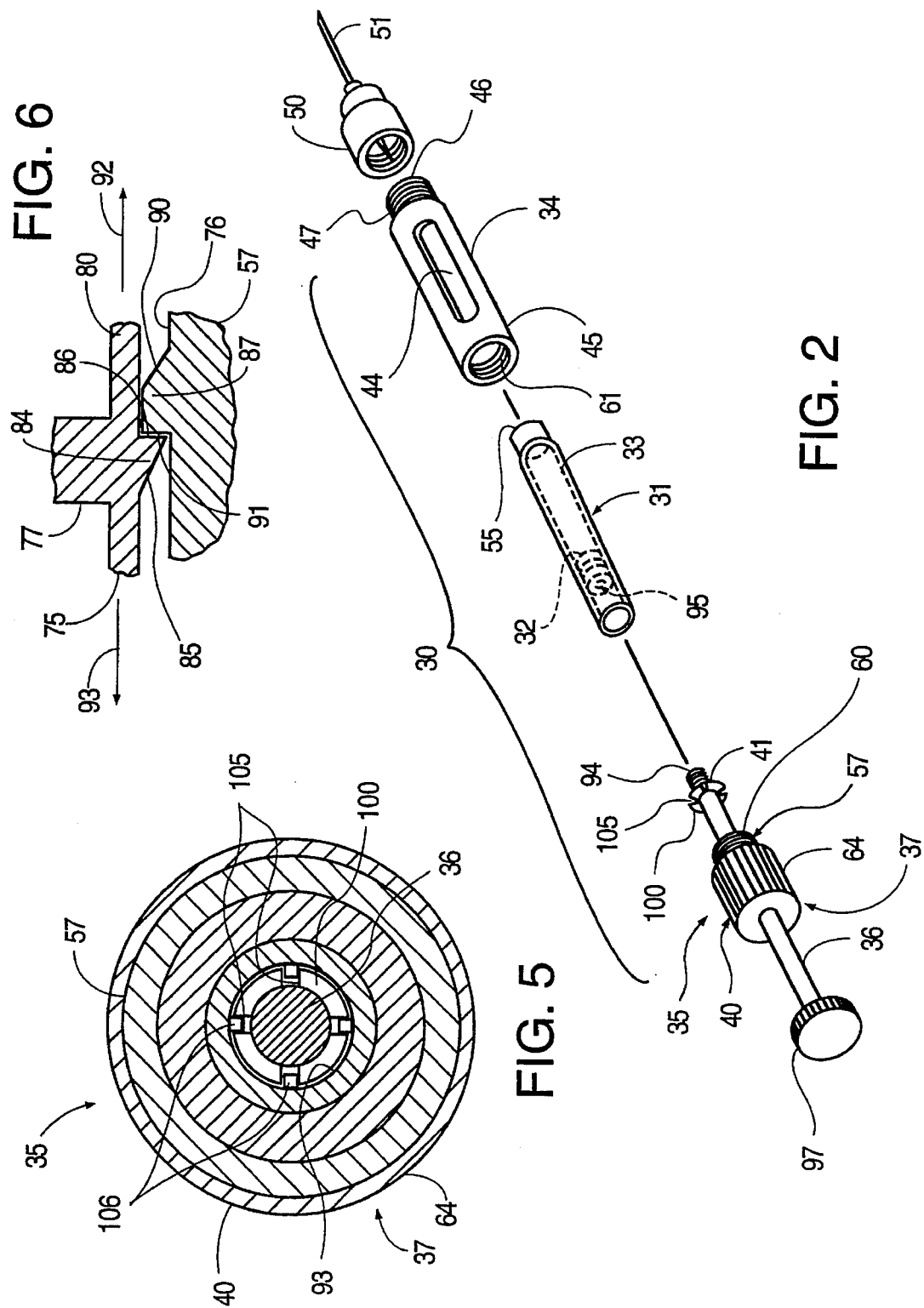

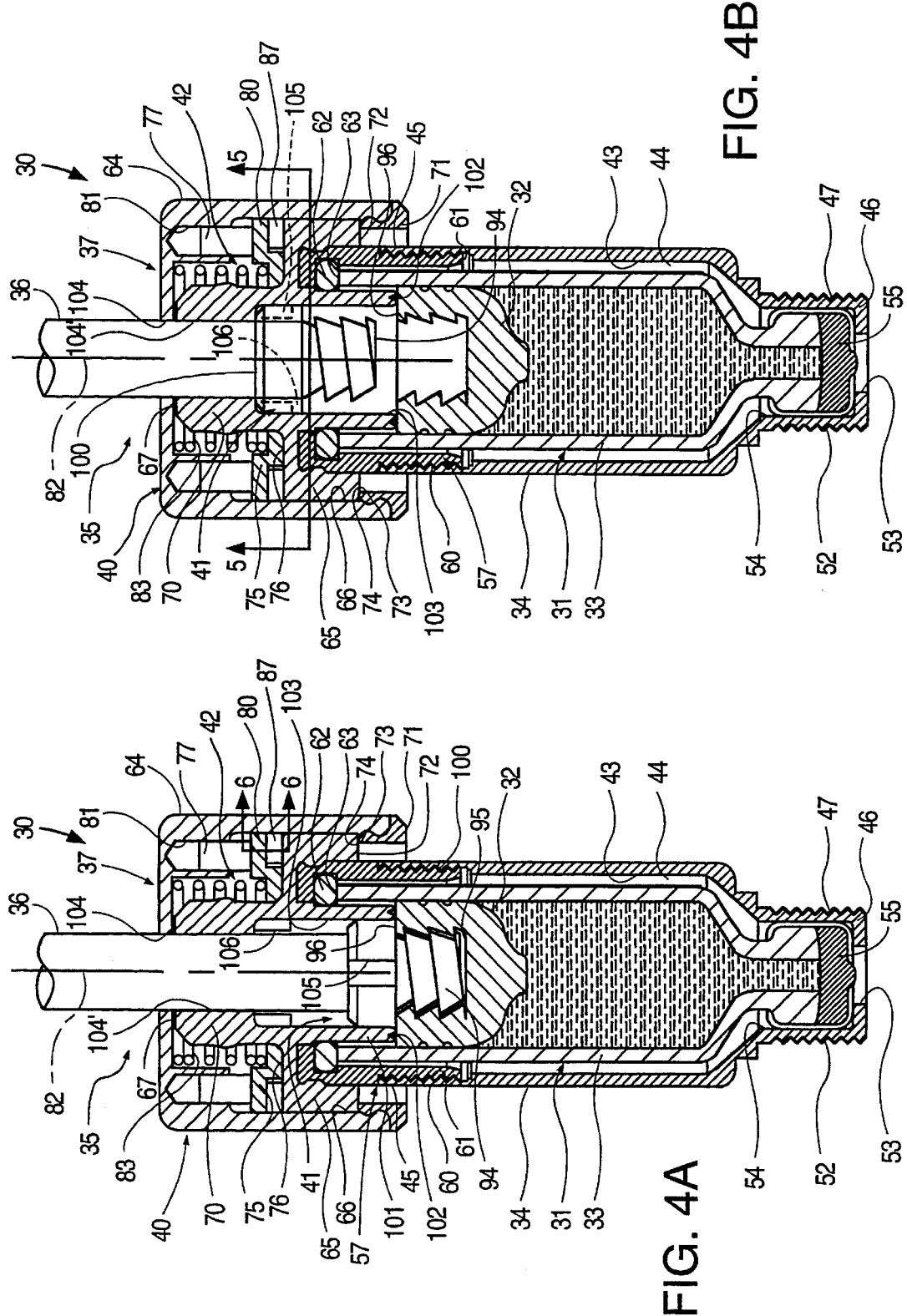

INJECTION PEN SOLUTION TRANSFER APPARATUS AND METHOD

TECHNICAL FIELD

The present invention relates, generally, to medicament delivery apparatus, and, more particularly, relates to injection pen apparatus.

BACKGROUND ART

Self-administered subcutaneous or intramuscular injections have long been available for those persons, such as diabetics, requiring fixed or measured amounts of medicaments. Prior to recent developments, self-administered injections were rendered using common syringes adapted to receive cartridges of premeasured doses of medicament. It is often the case, however, that these individuals require more than one dose per day where each dose requires a different amount of medicament. While these common syringe devices are adequate to deliver premeasured doses, delivery of amounts less than the premeasured dose tend to be highly inaccurate, a result which may be potentially dangerous.

More recently, injection pens have been developed which permit the recipient to accurately adjust the volume or amount of medicament dispensed from the prefilled cartridge positioned in the injection pen. Briefly, as illustrated in FIG. 1, these prefilled medicament cartridges 10 to be placed in injection pen 11 contain the medicament solution therein. One end 12 of the cartridge is formed to be pierced and penetrated by a needle assembly 13 for dispensing therefrom, while the other opposite end 14 thereof is sealed by a slidable plunger 15. By accurately controlling the sliding movement of the plunger toward the pierceable end 12, the volume and amount medicament expelled through the needle assembly can be controlled.

Typically, these injection pen assemblies 11 include a sleeve member 16 formed to receive the prefilled cartridge 10 through an open end 17 thereof. FIG. 1 illustrates that an opposite end 20 of the sleeve member 16 is generally mounted to double-sided needle assembly 13 formed for subcutaneous or intramuscular injection of medicament from the cartridge assembly. Removably mounted to sleeve open end 17 is a dispensing assembly 21 operably coupled to cartridge plunger 15 for manual manipulation thereof.

A dispensing housing 22 of dispensing assembly 21 is formed to mount directly to sleeve 16, via mating threads 23, which seats cartridge 10 in sleeve 16 and into engagement with needle assembly 13. A plunger rod 24 having a plunger head 18, which abuts a backside 25 of the plunger, is mounted to dispensing housing for axial movement in a direction toward the needle assembly. As mentioned, by governing the axial movement of the plunger rod, the displacement of the plunger can be controlled, thereby controlling the delivery of the medicament. Typical of these injection pen assemblies may be found in U.S. Pat. Nos. 4,413,760; 4,592,745; 4,950,246; 5,226,895; and 5,226,896.

While these injection pen devices are adequate to dispense medicaments from prefilled cartridges, certain medicament solutions must be prepared daily, weekly or biweekly because they have short storage shelf lives in solution. For example, certain medicaments may be more stable when stored in a solid or semi-solid form. Just before infusion or injection into the recipient, these solid/semi-solid medicaments are dissolved in a diluent. Hence, prefilled cartridges containing these types of medicaments are not always feasible nor are available.

To overcome these deficiencies, self-administered loading devices have been developed which are capable of loading injection pen cartridges with medicament solution. Typically, similar to an injection pen, a filling sleeve (i.e., analogous to sleeve member 16 in FIG. 1) is provided which is formed to receive an empty medicament cartridge through one end, while an opposite end thereof engages a needle assembly. To seat the empty cartridge in the filling sleeve and to control filling of the cartridge, a plunger rod assembly is provided which is positively coupled to both the filling sleeve and to the cartridge plunger. Similar to dispensing housing 22 of the injection pen (FIG. 1), the plunger rod assembly includes a filling housing removably coupled to the filling sleeve. Further, the plunger rod assembly includes a slidable displacement rod which also contacts the backside of the cartridge plunger.

To enable filling of the empty cartridge, in which the needle assembly is in communication with a medicament reservoir, the displacement rod must be capable of withdrawing the cartridge plunger in a direction away from the needle assembly end. This is accomplished by positively coupling a distal end of the displacement rod to the cartridge plunger, unlike the injection pen. Thus, movement of the plunger can be manually attained and controlled both toward and away from the needle assembly to effect dispensing and filling, respectively, of the cartridge.

Once the cartridge has been filled, the prior art plunger rod assembly must be removed from its filling sleeve in order to remove the filled cartridge so that it can be reinserted for use in injection pen 11 of FIG. 1. Both the dispensing housing and the displacement rod of the plunger rod assembly must be uncoupled from the filling sleeve and from the cartridge plunger, respectively. As a result of this design, the loading device operator often forgets to uncouple the displacement rod from the cartridge plunger before the plunger rod assembly is separated from the filling sleeve and cartridge. In this event, the plunger, still coupled to the end of the displacement rod, will be inadvertently pulled out of the filled cartridge which may contaminate the medicament solution or result in spillage therefrom. Ultimately, costly medicament is wasted.

DISCLOSURE OF INVENTION

Accordingly, it is an object of the present invention to provide an injection pen solution transfer device and method which prevents inadvertent removal of a plunger from a cartridge assembly.

Another object of the present invention is to provide an injection pen solution transfer device and method for an injection pen which facilitates removal of the plunger rod from a filling sleeve.

Still another object of the present invention is to provide an injection pen solution transfer device and method which is capable of filling the cartridge assembly with a medicament solution.

Yet another object of the present invention is to provide an injection pen solution transfer device and method which reduces waste of the medicament solution.

Another object of the present invention is to provide an injection pen solution transfer device and method which mounts to the existing cartridge sleeve of the injection pen.

It is a further object of the present invention to provide an injection pen solution transfer device and method which is durable, compact, easy to maintain, has a minimum number of components, and is easy to use by unskilled personnel.

In accordance with the foregoing objects, the present invention provides an injection pen apparatus for medicament injection including a medicament cartridge assembly formed to receive and contain a medicament therein, and having a movable plunger slidably mounted in the cartridge assembly. A holding sleeve is provided which is dimensioned to receive the medicament cartridge assembly therein which mates with a solution transfer device including an axially movable displacement rod. The injection pen apparatus further includes a coupling mechanism removably coupling the solution transfer device to both the plunger and to the holding sleeve and is formed to slidably and rotatably support the displacement rod along an axial direction thereof. A sleeve mounting assembly removably mounts the coupling mechanism to the holding sleeve. A locking device is included which is formed and dimensioned to require joining of the displacement rod relative to the sleeve mounting assembly after uncoupling of the rod from the plunger and before uncoupling of a remainder of the solution transfer device from the holding sleeve.

A method for removal of the solution transfer device from an injection pen assembly comprises the steps of preventing uncoupling of the solution transfer device from the sleeve until the displacement rod is uncoupled from the plunger to prevent premature removal of the plunger from the cartridge; uncoupling the displacement rod from the plunger; and after the uncoupling step, removing a remainder of the solution transfer device from the sleeve.

BRIEF DESCRIPTION OF THE DRAWING

The assembly of the present invention has other objects and features of advantage which will be more readily apparent from the following description of the best mode of carrying out the invention and the appended claims, when taken in conjunction with the accompanying drawing, in which:

FIG. 2 is an exploded top perspective view of a solution transfer device constructed in accordance with the present invention together with a cartridge and sleeve member of an injection pen assembly.

FIGS. 4A and 4B are a series of enlarged, fragmentary, front elevation views, in cross-section partially broken away, of the solution transfer device of FIG. 3 and illustrating proper removal thereof from the cartridge and injection pen sleeve.

FIG. 5 is a bottom plan view, in cross-section, of a locking device of the present invention taken substantially along the plane of line 5—5 in FIG. 4B.

FIG. 6 is an enlarged, fragmentary, side elevation view, in cross-section, of the locking engagement between a ramped portion and a pawl member of a ratchet mechanism of the present invention taken substantially along the plane of line 6—6 in FIG. 4A.

BEST MODE OF CARRYING OUT THE INVENTION

Figures 1, 3:
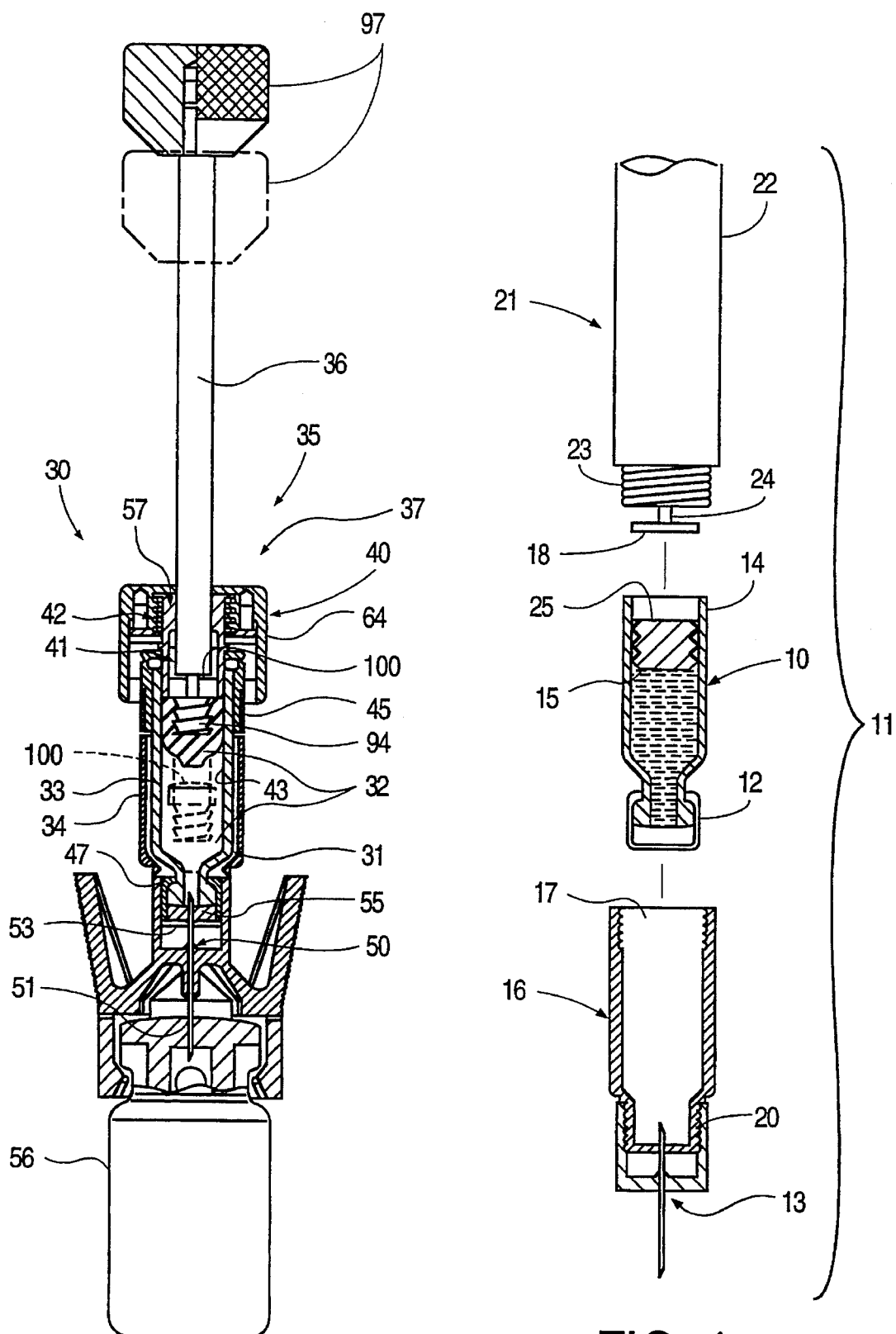
FIG. 1 is an exploded, fragmentary, front elevation view, in partial cross-section, of a prior art injection pen assembly retaining a pre-filled medicament cartridge therein.
FIG. 3 is an enlarged front elevation view, in partial cross-section, of the solution transfer device of FIG. 2 mounted to the cartridge and sleeve member of the injection pen assembly.

While the present invention will be described with reference to a few specific embodiments, the description is illustrative of the invention and is not to be construed as limiting the invention. Various modifications to the present invention can be made to the preferred embodiments by those skilled in the art without departing from the true spirit and scope of the invention as defined by the appended claims. It will be noted here that for a better understanding, like components are designated by like reference numerals throughout the various figures.

Attention is now directed to FIG. 2 where an injection pen cartridge loading device, generally designated 30, is shown for medicament injection including a medicament cartridge assembly, generally designated 31, formed to receive and contain a medicament therein. The cartridge assembly includes a movable plunger 32 slidably mounted in a hollow cartridge 33 which is formed to expel or draw medicament from or into the cartridge through manual manipulation of the plunger. A filling sleeve or cartridge holding sleeve, generally designated 34, is provided which is dimensioned to receive and hold medicament cartridge assembly 31 therein for alignment and support. The injection pen cartridge loading device 30 further includes a solution transfer device, generally designated 35, having a movable displacement rod 36 slidably and rotatably supported along an axial direction thereof. A coupling mechanism 37 removably couples solution transfer device 35 to both cartridge plunger 32 and to holding sleeve 34, and includes a sleeve mounting assembly, generally designated 40, removably mounting the coupling mechanism to the holding sleeve. A locking device 41 is included which is formed and dimensioned to require joining of displacement rod 36 relative sleeve mounting assembly 40 after uncoupling of the rod from plunger 32 and before uncoupling of a remainder of solution transfer device 35 from the holding sleeve.

Accordingly, as shown in FIG. 4B, the sleeve mounting assembly of coupling mechanism 37 cannot be uncoupled or separated from holding sleeve 34 (via ratchet mechanism 42 to be described below) until displacement rod 36 has been uncoupled from cartridge plunger 32. Upon detachment therebetween, the locking device disposed between the displacement rod 36 and sleeve mounting assembly 40 (FIGS. 4B and 5) rotationally joins the two components together. Such joining permits removal of the sleeve mounting assembly, and hence, the coupling mechanism, from the holding sleeve. This configuration prevents inadvertent removal of cartridge plunger 32 from cartridge 33 since coupling mechanism 37 prevents removal of solution transfer device 35 from holding sleeve 34 before the displacement rod has been detached or uncoupled from the plunger.

In the preferred embodiment, holding sleeve 34 of the solution transfer device dimensioned substantially similar to sleeve member 16 of the injection pen assembly 11 shown in FIG. 1. Therefore, holding sleeve 34 is preferably interchangeable with sleeve member 16 for convenience. Thus, once cartridge assembly 31 has been loaded and the solution transfer device has been removed from holding sleeve 34, the filled cartridge assembly need not be removed from the holding sleeve since the dispensing housing 22 (FIG. 1) of the injection pen assembly may be mounted directly to the holding sleeve to dispense the medicament solution from the cartridge assembly.

Turning now to FIGS. 3, 4A and 4B, the injection pen cartridge loading device 30 of the present invention will be described in more detail. As mentioned, the loading device includes a holding sleeve 34 substantially similar in shape and dimension to the sleeve member of the injection pen assembly of FIG. 1. Hence, holding sleeve 34 is preferably provided by an elongated cylindrical member having an interior wall 43 defining a cavity 44 formed for receipt of the cartridge assembly 31 through an open end 45 thereof. An opposite end 46 (FIGS. 4A and 4B) of the holding sleeve 34 is dimension to removably mount to a double-sided needle assembly, via threads 47, such as the dispensing needle assembly 13 of FIGS. 1 and 2, or the needle assembly 50 of a transfer needle 51 shown in FIG. 3. Sleeve opposite end 46 further includes a shoulder portion 52 forming a receiving aperture 53 which extends into sleeve cavity 44. Through receiving aperture 53, access to the medicament solution contained in cartridge 33 may be attained by needle assembly 50.

Sleeve cavity 44 includes a lower channel portion 54 tapering inwardly and formed to snugly receive a frangible nose portion 55 of cartridge assembly 31. FIGS. 4A and 4B best illustrate that the cartridge nose portion is aligned and retained against shoulder portion 52 upon mounting of the solution transfer device to the holding sleeve. Accordingly, when transfer needle 51 is mounted to sleeve opposite end 46, needle assembly 50 which is aligned with receiving aperture 53 pierces through cartridge frangible nose portion 55 to access the medicament solution retained therein.

Incidently, transfer needle 51 is commonly known in the field and does not constitute a novel feature of the present invention. FIG. 3 illustrates that the transfer needle is formed to removably mount to a medicament reservoir vial 56 for loading the cartridge assembly with medicament. Typically, reservoir vial 56 either contains pre-prepared medicament solution or a solid/semi-solid medicament requiring dissolution with a diluent. In the latter situation, the diluent may be provided in a prefilled cartridge assembly which is expelled therefrom into reservoir vial 56 through needle assembly 50 by manual manipulation of cartridge plunger 32. Subsequently, after preparation of the medicament solution, solution transfer device 35, mounted transfer needle 51 and reservoir vial 56 are turned upsidedown, as a unit, so that the medicament solution can drawn or loaded through needle assembly 50 into cartridge assembly 31 by employing solution transfer device 35.

As above-indicated, the coupling mechanism is formed to require uncoupling of the displacement rod from the cartridge plunger before uncoupling from holding sleeve 34. FIG. 3 illustrates that sleeve mounting assembly 40 slidably and rotatably supports displacement rod 36 along an axial direction thereof for aligned reciprocating movement of the cartridge plunger in the cartridge when coupled to the rod (phantom lines in FIG. 3). The sleeve mounting assembly includes an inner mounting member 57 formed and dimensioned to mount to the holding sleeve. Inner mounting member 57 includes outward facing threads 60 which mate with holding sleeve threads 61 provided in interior wall 43 proximate sleeve open end 45. Through manual manipulation of coupling mechanism 37, inner mounting member 57 mounts solution transfer device 35 to holding sleeve 34 for operation thereof. Likewise, before the coupling mechanism can be separated from the holding sleeve, the threads of the inner mounting member must be unscrewed from the threads of the holding sleeve.

Referring back to FIGS. 4A and 4B, it can be viewed that inner mounting member 57 includes a washer 62 formed and positioned to abut a top edge 63 of cartridge 33 upon coupling of the inner mounting member to the holding sleeve. As the sleeve mounting assembly is mounted to the holding sleeve, washer 62 increasingly engages top edge 63 to urge cartridge nose portion 55 into cavity channel portion 54 for alignment therebetween.

In accordance with the present invention, sleeve mounting assembly 40 further includes an outer cap member 64 (FIGS. 2, 4A and 4B) formed to substantially surround inner mounting member 57 such that the inner mounting member cannot be manually operated or accessed when the sleeve mounting assembly is mounted to the holding sleeve. Thus, outer cap member 64 acts as a shield which eliminates physical access to the inner mounting member.

As best viewed in FIGS. 4A and 4B, sleeve mounting assembly 40 includes a ratchet mechanism, generally designated 42, operably positioned between the inner mounting member and the outer cap member. Ratchet mechanism 42 rotationally couples outer cap member 64 to inner mounting member 57 in one rotational direction (preferably clockwise) in a manner permitting mounting of the inner mounting member to the sleeve member upon manual engagement with the cap member. However, the ratchet mechanism is further configured to prevent rotational coupling between the inner mounting member and the cap member, in the other rotational direction (preferably counterclockwise), upon manual engagement of the cap member. Accordingly, ratchet mechanism 42 permits torque transfer to inner mounting member 57 for mounting of sleeve mounting assembly 40 to holding sleeve 34 (i.e., clockwise rotational engagement with the cap member), while further preventing torque transfer between the same to prevent removal from the holding sleeve (i.e., counterclockwise rotational engagement with the cap member).

To provide relative rotational engagement between inner mounting member 57 and cap member 64, the inner mounting member includes an annular bearing portion 65 (FIG. 4B) situated in bearing contact with an inward facing wall 66 of the cap member. The cap member further seats against an upper surface 67 of a hub portion 70 of the inner mounting member, and is retained in place through a closure ring 71 which abuts bottom surface 72 of bearing portion 65. The closure ring includes an annular ledge 73 formed to snap fit together with a ring groove 74, provided in inward facing wall 66, for mating engagement therebetween.

While the ratchet mechanism 42 may be provided by any ratchet assembly commonly used in the field, preferably, ratchet mechanism 42 includes a ratchet ring 75 in abutting rotational contact with a support flange 76 extending outwardly from hub portion 70 upon which annular bearing portion 65 is mounted. The ratchet ring includes at least one torque transfer pin 77 extending upwardly from an outer flange portion 80 of ring 75. Transfer pin 77 is formed to slidably engage a corresponding pin receiving socket 81 provided in cap member 64. Accordingly, transfer pin 77 and receiving socket 81 cooperate to transfer torque manually exerted on cap member about axis 82 thereof to ratchet ring 75. Socket 81 and transfer pin 77 further permit vertical movement of the ratchet ring relative the cap member along an axial direction thereof. The ratchet mechanism 42, lastly, includes a compression spring 83 positioned between the cap member and the ratchet ring which biases the ring in abutting contact with support flange 76.

Ratchet ring 75 includes at least one tooth 84 (FIG. 6) extending downwardly from outer flange portion 80 of the ring. In the preferred embodiment, the ratchet ring provides a plurality of teeth extending circumferentially about axis 82. Each tooth 84 includes a ramped surface 85 and an abutting surface 86. Similarly, the inner mounting member 57 includes a corresponding pawl member 87 having a ramped surface 90 and a contact surface 91 situated to abut against and contact the opposite facing tooth abutting surface 86 as cap member 64 is manually rotated in the clockwise direction (arrow 92 in FIG. 6) about axis 82. Upon abutting engagement between the tooth abutting surface and the ring contact surface, torsional force manually exerted on the cap member can be transmitted to the inner mounting member during mounting of the solution transfer device to the holding sleeve.

In accordance with the present invention, as mentioned, ratchet mechanism is further configured to prevent removal of the inner mounting member from the holding sleeve. Upon manual counterclockwise rotation of cap member 64 relative inner mounting member 57 (arrow 93 in FIG. 6), the tooth ramped surface 85 slidably contacts pawl ramped surface 90 to move tooth 84 move up and over pawl member 87. During sliding contact, as tooth 84 moves up pawl ramped surface 90, torque transfer pin is moved axially along socket 81. The cap member, thus, is permitted to rotate counterclockwise without interference so that the torsional force manually exerted on the cap member is not transmitted to the inner mounting member. Accordingly, sleeve mounting assembly cannot be manually removed from the holding sleeve 34 through engagement with outer cap member 64.

FIGS. 4A and 4B illustrate that coupling mechanism 37 further includes a threaded stud 94 on the distal end of displacement rod 36 formed for mating engagement with a threaded recess 95 defined in the backside surface 96 of cartridge plunger 32. Through manual rotation of displacement rod 36 (via, knob 97 (FIGS. 2 and 3)) about axis 82, in the clockwise direction, threaded stud 94 increases engagement with threaded recess 95 until a locking ring 100 of locking device 41 abuts against plunger backside surface 96. Continued threading of stud 94 into recess 95 causes plunger 32 to radially swell outwardly from axis 82 to increasingly engage the interior walls of cartridge 33. As a result, the seal integrity therebetween is also intensified. It will be understood, of course, that the displacement rod may be formed with the threaded recess while the cartridge plunger provides the threaded stud without departing from the true spirit and nature of the present invention.

Inner mounting member 57 further includes a plunger engaging portion 101 extending downwardly from hub portion 70 toward the cartridge plunger. A bottom edge 102 of plunger engaging portion 101 engages plunger backside surface 96 when cartridge assembly 31 is loaded to capacity, as shown in FIGS. 4A and 4B. When stud 94 is unscrewed from threaded recess 95, the bottom edge of the plunger engaging portion contacts the cartridge plunger to prevent rotation thereof in the cartridge to facilitate removal. Preferably, bottom edge 102 is serrated or textured to enhance frictional gripping with the plunger backside surface 96.

Plunger engaging portion 101 further defines a hub chamber 103 formed to slidably receive locking device 41 and threaded stud 94 therein. Chamber 103 must be of a sufficient axial length to permit interengagement of the locking device components (to be described below) which rotationally joins the displacement rod with the inner mounting member of the sleeve mounting assembly. Such joining permits rotational disengagement between the threads 61, 60 of the corresponding holding sleeve 34 and inner mounting member 57, respectively.

Briefly, sleeve mounting assembly 40 of coupling mechanism 37 includes rod receiving apertures 104, 104' axially aligned along axis 82 and extending through cap member 64 and mounting member hub portion 70, respectively, into chamber 103. Receiving aperture 104, 104' is formed to axially receive and slidably support the displacement rod therein so that rod 36 can reciprocate along an axial direction thereof relative sleeve mounting assembly 40 (FIG. 3) during manual movement of cartridge plunger 32.

FIGS. 4A, 4B and 5 best illustrate that locking device 41 includes locking ring 100 slidably received in hub chamber 103 upon uncoupling of threaded stud 94 from threaded recess 95. The locking device includes at least one keyway 105 formed in locking ring 100 for mating interengagement with a key member 106 of inner mounting member 57 extending into chamber 103. Accordingly, to remove solution transfer device 35 from holding sleeve 34, after loading of cartridge assembly 31, threaded stud 94 must first be disengaged from threaded recess 95. As mentioned, manual counterclockwise rotation of cap member 64 will not disengage the inner mounting member from the holding sleeve due to ratchet mechanism 42. Once the threaded stud has been detached, locking ring 100 is retracted into hub chamber 103 along axis 82, via displacement rod 36, and rotated until keyway 105 is aligned with key member 106. Interengagement between the key member and the keyway of the locking device rotationally joins the displacement rod with the inner mounting member. Hence, manual counterclockwise rotational motion of the rod transfers torque, via locking device 41, to sleeve mounting assembly 40 (FIG. 4B). Subsequently, solution transfer device can be separated from both the holding sleeve and the cartridge assembly without inadvertent removal of the cartridge plunger from the cartridge assembly.

In the preferred form, as shown in FIG. 5, locking ring 100 provides four keyways 105 while inner mounting member 57 includes four corresponding key member 106 for interengagement therewith. The locking ring, mounted just above threaded stud 94, also prevents separation of displacement rod 36 from sleeve mounting assembly 40. Further, it will be appreciated that locking ring 100 could provide the key member while the inner mounting member provides the keyway without departing from the true spirit and nature of the present invention.

In another aspect of the present invention, a method for removal of the solution transfer device from the injection pen holding sleeve comprises the steps of preventing uncoupling of solution transfer device 35 from holding sleeve 34 until displacement rod 36 is uncoupled from cartridge plunger 32 to prevent premature removal of the plunger from cartridge assembly 31; uncoupling displacement rod 36 from cartridge plunger 32; locking rotational displacement of rod 36 relative inner mounting member 57 through locking device 41 disposed therebetween; and after the locking step, removing sleeve mounting assembly 40 of solution transfer device 35 from holding sleeve 34.

What is claimed is:

1. In an injection pen device for medicament injection including a holding sleeve dimensioned to receive a medicament cartridge assembly therein, a medicament cartridge assembly mounted in said holding sleeve and formed to receive and contain a medicament therein, and having a movable plunger slidably mounted in said cartridge assembly, a solution transfer device being removably coupled to both said plunger and to said holding sleeve, and including a movable displacement rod, wherein the improvement comprises:

said solution transfer device being coupled to said plunger and to said holding sleeve by a coupling mechanism formed to require uncoupling of said displacement rod from said plunger before uncoupling of a remainder of said solution transfer device from said holding sleeve.

2. The injection pen device as defined in claim 1 wherein, said coupling mechanism includes a sleeve mounting assembly slidably and rotatably supporting said displacement rod along an axial direction thereof for aligned reciprocating movement of said plunger in said cartridge assembly, said sleeve mounting assembly further being formed to removably mount said coupling mechanism to said holding sleeve.

3. The injection pen device as defined in claim 2 wherein, said coupling mechanism further includes a locking device disposed between said displacement rod and said sleeve mounting assembly for locking engagement therebetween upon uncoupling of said displacement rod from said plunger.

4. The injection pen device as defined in claim 3 wherein, said locking device includes at least one key member mounted to one of said displacement rod and said rod mounting assembly, and providing at least one keyway in the other of said displacement rod and said sleeve mounting assembly formed to matingly receive said one key member therein.

5. The injection pen device as defined in claim 4 wherein, said locking device includes a ring member defining said one keyway and protruding outwardly from said displacement rod proximate a distal end thereof, and said one key member being mounted to said sleeve mounting assembly and aligned to engage said one keyway.

6. The injection pen device as defined in claim 5 wherein, said coupling mechanism further includes a threaded stud provided by one of said displacement rod and said plunger, and a threaded recess defined in the other of said displacement rod and said plunger, and formed to matingly engage said threaded stud therein to provide removable mounting therebetween.

7. The injection pen device as defined in claim 6 wherein, said threaded stud is provided on a distal end of said displacement rod, and said threaded recess is provided by said plunger.

8. The injection pen device as defined in claim 7 wherein, said sleeve mounting assembly defines a chamber formed to slidably receive said ring member and said threaded stud therein, and further being sufficient dimensioned to permit locking engagement of said one key member with said one keyway after disengaging separation of said threaded stud from said threaded recess.

9. The injection pen device as defined in claim 2 wherein, said coupling mechanism further includes a threaded stud provided by one of said displacement rod and said plunger, and a threaded recess defined in the other of said displacement rod and said plunger, and formed to matingly engage said threaded stud therein to provide removable mounting therebetween.

10. The injection pen device as defined in claim 9 wherein, said threaded stud is provided on a distal end of said displacement rod, and said threaded recess is provided by said plunger.

11. The injection pen device as defined in claim 1 wherein, said coupling mechanism further includes a sleeve mounting assembly slidably and rotatably supporting said displacement rod along an axial direction thereof for aligned reciprocating movement of said plunger in said cartridge assembly, said sleeve mounting assembly including:
  (A) an inner mounting member formed and dimensioned to mount said holding sleeve,
  (B) an outer cap member substantially surrounding said inner mounting member, and
  (C) a ratchet mechanism positioned between said mounting member and said cap member in a manner permitting mounting of said mounting member to said holding sleeve through manual engagement with said cap member, said ratchet mechanism further being formed to prevent removal of said mounting member from said holding sleeve through manual engagement with said cap member.

12. The injection pen device as defined in claim 11 wherein, said coupling mechanism further includes a locking device disposed between said displacement rod and said inner mounting member for locking engagement therebetween upon uncoupling of said displacement rod from said plunger.

13. The injection pen device as defined in claim 12 wherein, said inner mounting member defines a chamber formed to slidably receive said locking device therein, and further being sufficiently dimensioned to permit locking engagement of said locking device after uncoupling of said displacement rod from said plunger.

14. The injection pen device as defined in claim 13 wherein, said locking device includes at least one key member extending from said inner mounting member into said chamber proximate a rear portion thereof, and a ring member protruding outwardly from said displacement rod proximate a distal end thereof and defining at least one keyway formed to matingly receive said one key member therein for said locking engagement therebetween.

15. The injection pen device as defined in claim 13 wherein, said coupling mechanism further including a rod receiving aperture formed to axially receive and slidably support said displacement rod therein, said receiving aperture extending through both said outer cap member and said inner mounting member and terminating in and axially aligned with said chamber.

16. The injection pen device as defined in claim 11 wherein, said coupling mechanism further includes a threaded stud provided by one of said displacement rod and said plunger, and a threaded recess defined in the other of said displacement rod and said plunger, and formed to matingly engage said threaded stud therein to provide removable mounting therebetween.

17. The injection pen device as defined in claim 16 wherein, said threaded stud is provided on a distal end of said displacement rod, and said threaded recess is provided by said plunger.

18. The injection pen device as defined in claim 11 wherein, said inner mounting member includes a plunger engaging portion extending downwardly toward said plunger, said engaging member formed to engage said plunger to resist relative rotational motion therebetween during uncoupling of said displacement rod from said plunger.

19. The injection pen device as defined in claim 18 wherein, said plunger engaging portion includes a serrated edge portion formed to engage said plunger member.

20. The injection pen device as defined in claim 11 wherein, said inner mounting member includes a threaded portion formed and dimensioned to threadably engage an opposing threaded portion provided by said holding sleeve.

21. The injection pen device as defined in claim 11 wherein, said cartridge assembly is dimensioned such that an edge portion thereof, facing toward said coupling mechanism, extends beyond a distal end of said holding sleeve when said cartridge assembly is mounted in said holding sleeve, and said inner mounting member includes a shoulder portion facing toward said cartridge edge portion for engagement therewith to form an air tight seal when said mounting member is mounted to said holding sleeve.

22. The injection pen device as defined in claim 21 wherein, said rod mounting assembly further includes a washer disposed between said mounting member shoulder portion and said cartridge edge portion.

23. An injection pen apparatus for medicament injection comprising:

a medicament cartridge assembly formed to receive and contain a medicament therein, and having a movable plunger slidably mounted in said cartridge assembly;

a holding sleeve dimensioned to receive said medicament cartridge assembly therein;

a solution transfer device including an axially movable displacement rod;

a coupling mechanism removably coupling said solution transfer device to both said plunger and to said holding sleeve and formed to slidably and rotatably support said displacement rod along an axial direction thereof, said coupling mechanism including a sleeve mounting assembly removably mounting said coupling mechanism to said holding sleeve, and a locking device formed and dimensioned to require joining of said displacement rod relative said sleeve mounting assembly after uncoupling of said displacement rod from said plunger and before uncoupling of a remainder of said solution transfer device from said holding sleeve.

24. The injection pen device as defined in claim 23 wherein, said sleeve mounting assembly includes:
(A) an inner mounting member formed and dimensioned to mount said holding sleeve,
(B) an outer cap member substantially surrounding said inner mounting member, and
(C) a ratchet mechanism positioned between said mounting member and said cap member in a manner permitting mounting of said mounting member to said holding sleeve through manual engagement with said cap member, said ratchet mechanism further being formed to prevent removal of said mounting member from said holding sleeve through manual engagement with said cap member.

25. The injection pen device as defined in claim 24 wherein, said locking device includes at least one key member mounted to one of said displacement rod and said rod mounting assembly, and at least one keyway provided in the other of said displacement rod and said sleeve mounting assembly and formed to matingly receive said one key member therein.

26. The injection pen device as defined in claim 25 wherein, said locking device includes a ring member defining said one keyway and protruding outwardly from said displacement rod proximate a distal end thereof, and said one key member being mounted to said sleeve mounting assembly and aligned to engage said one keyway.

27. The injection pen device as defined in claim 26 wherein, said coupling mechanism further includes a threaded stud provided on a distal end of said displacement rod, and a threaded recess defined by said plunger and formed to matingly engage said threaded stud therein to provide removable mounting therebetween.

28. The injection pen device as defined in claim 27 wherein, said sleeve mounting assembly defines a chamber formed to slidably receive said ring member and said threaded stud therein, and further being sufficient dimensioned to permit locking engagement of said one key member with said one keyway after disengaging separation of said threaded stud from said threaded recess.

29. A method for removing a solution transfer device, having a movable displacement rod, from an injection pen device formed for medicament injection, the pen injection device including a medicament cartridge assembly formed to receive and contain a medicament therein and having a movable plunger slidably mounted in said cartridge assembly, a holding sleeve dimensioned to receive said medicament cartridge assembly therein, and a coupling mechanism removably coupling said solution transfer device to said plunger and to said holding sleeve, the method comprising the steps of:

preventing uncoupling of said solution transfer device from said holding sleeve until said displacement rod is uncoupled from said plunger to prevent premature removal of said plunger from said cartridge;

uncoupling said displacement rod from said plunger; and after said uncoupling step, removing a remainder of said solution transfer device from said holding sleeve.

30. The method of claim 29 wherein, after said uncoupling step and before said removing step, locking rotational displacement of said rod relative said coupling mechanism through a locking device disposed therebetween.

31. The method of claim 29 wherein, said uncoupling step is accomplished by unscrewing a threaded stud provided by one of said displacement rod and said plunger from a threaded recess defined in the other of said displacement rod and said plunger, and formed to matingly engage said threaded stud therein to provide removable mounting therebetween.

32. The method of claim 30 wherein, said locking step is accomplished by engaging at least one key member mounted to one of said displacement rod and said sleeve mounting assembly with at least one keyway provided in the other of said displacement rod and said sleeve mounting assembly and formed to matingly receive said one key member therein.

* * * * *